US012503725B2

(12) United States Patent
Li et al.

(10) Patent No.: US 12,503,725 B2
(45) Date of Patent: Dec. 23, 2025

(54) NUCLEIC ACID ISOTHERMAL AMPLIFICATION COLLOIDAL GOLD TEST DEVICE

(71) Applicants: Sichuan Tianyi Guifeng Biomedical Technology Co., Ltd, Chengdu (CN); Sichuan X-codon Technology Co., Ltd, Chengdu (CN)

(72) Inventors: Yaoheng Li, Chengdu (CN); Tao Lu, Chengdu (CN)

(73) Assignees: Sichuan Tianyi Guifeng Biomedical Technology Co., Ltd, Chengdu (CN); Sichuan X-codon Technology Co., Ltd, Chengdu (CN)

( * ) Notice: Subject to any disclaimer, the term of this patent is extended or adjusted under 35 U.S.C. 154(b) by 542 days.

(21) Appl. No.: 18/152,657

(22) Filed: Jan. 10, 2023

(65) Prior Publication Data

US 2024/0158841 A1 May 16, 2024

(30) Foreign Application Priority Data

Nov. 14, 2022 (CN) ........................ 202223021264.4

(51) Int. Cl.
*C12Q 1/6844* (2018.01)
*B01L 3/00* (2006.01)

(52) U.S. Cl.
CPC ...... *C12Q 1/6844* (2013.01); *B01L 3/502715* (2013.01); *B01L 2200/16* (2013.01); *B01L 2300/0832* (2013.01); *B01L 2300/0848* (2013.01); *B01L 2300/0861* (2013.01); *B01L 2300/1805* (2013.01)

(58) Field of Classification Search
CPC ........... C12Q 1/6844; B01L 2300/0672; B01L 2300/0825; B01L 2300/087
See application file for complete search history.

(56) References Cited

FOREIGN PATENT DOCUMENTS

| | | | |
|---|---|---|---|
| CN | 205115443 U | * | 3/2016 |
| CN | 114807320 A | | 7/2022 |
| CN | 115074420 A | | 9/2022 |

OTHER PUBLICATIONS

Google machine translation of CN205115443U, [retrieved on-line; retrieved from https://patents.google.com/patent/CN205115443U/en?oq=205115443; retrieval date: Aug. 21, 2025, pp. 1-17). (Year: 2015).*

* cited by examiner

*Primary Examiner* — Young J Kim

(57) ABSTRACT

The disclosure relates to the technical field of nucleic acid test, particularly to a nucleic acid isothermal amplification colloidal gold test device. The device comprises a lower seat and a reagent reaction module slideably arranged in the lower seat and comprising a reaction module shell, a reagent collection tube, a reagent reaction box, a solution box and a test paper installation assembly, the solution box is arranged at the bottom of the reaction module shell and located under the test paper installation assembly, the reagent reaction box is arranged on the solution box and partially located in the solution box, the reagent collection tube is arranged in the reaction module shell and the lower end is slideably matched with the reagent reaction box, and the test paper installation assembly is arranged in the reaction module shell and located outside the reagent collection tube.

9 Claims, 4 Drawing Sheets

NUCLEIC ACID ISOTHERMAL AMPLIFICATION COLLOIDAL GOLD TEST DEVICE

CROSS REFERENCE TO RELATED APPLICATIONS

This application claims foreign priority of Chinese Patent Application No. 202223021264.4, filed on Nov. 14, 2022 in the China National Intellectual Property Administration, the disclosures of all of which are hereby incorporated by reference.

TECHNICAL FIELD

The disclosure relates to the technical field of nucleic acid test, particularly to a nucleic acid isothermal amplification colloidal gold test device.

BACKGROUND OF THE PRESENT INVENTION

The existing target nucleic acid fragments are mainly detected by PCR (polymerase chain reaction). Commonly used PCR mainly includes general PCR that refers to a fact that a product is analyzed by using agarose gel electrophoresis after amplification of a target gene for qualitative analysis. There are multiple cycles of heating and cooling and PCR instruments.

Fluorescent quantitative PCR technology (qPCR): it is needed to add a fluorescent probe capable of indicating the process of a reaction into a reaction system so as to conduct quantitative detection through fluorescent signals. A PCR instrument is needed. Digital PCR (Dig-PCR): PCR and fluorescent signal detection are conducted subsequent to dispersing a sample by using a microfluidic or microdroplet method. A digital PCR instrument and corresponding chips and data analysis software are needed, so the cost is higher.

SUMMARY OF PRESENT INVENTION

The objective of the present disclosure is to provide a nucleic acid isothermal amplification colloidal gold test device in order to overcome the defects in the prior art.

The objective of the present disclosure is achieved by the following technical solution: a nucleic acid isothermal amplification colloidal gold test device, comprising a lower seat and a reagent reaction module, wherein the reagent reaction module is slideably arranged in the lower seat, the reagent reaction module comprises a reaction module shell, a reagent collection tube, a reagent reaction box, a solution box and a test paper installation assembly, the solution box is arranged at the bottom of the reaction module shell and located under the test paper installation assembly, the reagent reaction box is arranged on the solution box and partially located in the solution box, the reagent collection tube is arranged in the reaction module shell and the lower end is slideably matched with the reagent reaction box, and the test paper installation assembly is arranged in the reaction module shell and located outside the reagent collection tube.

Specifically, the top of the reagent collection tube is provided with a reagent collection tube plug.

Specifically, the bottom of the reagent collection tube is provided with a film, a pointed cone is arranged at the bottom inside the reagent reaction box, and the bottom of the reagent reaction box is provided with a leakage hole.

Specifically, the test paper installation assembly comprises a fixed tube and a sliding tube, the top of the fixed tube is fixed on the reaction module shell, and the upper end of the sliding tube is slideably arranged in the fixed tube.

Specifically, the upper end of the sliding tube is provided with two clips, the opposite outer sides of the two clips are provided with bulges, and an inner wall inside the fixed tube is provided with slots matched with the bulges.

Specifically, the middle of the sliding tube is provided with a stop block, a key is slideably arranged on the lower seat, and the key is matched with the stop block.

Specifically, an installation port is formed in a position of the solution box corresponding to the reagent installation assembly, two layers of installation films are arranged in the installation port, and a storage cavity is formed between two layers of the installation films.

Specifically, the lower seat comprises a seat bottom and a lower seat shell, a heat-conducting plate is arranged in the seat bottom, the heat-conducting plate is provided with a heating plate, the lower seat shell is arranged on the heat-conducting plate, and the bottom of the solution box is in contact with the heating plate and the heat-conducting plate.

Specifically, the nucleic acid isothermal amplification colloidal gold test device further comprises a housing and a connection cap, wherein the connection cap is arranged in the housing, the upper end of the reaction module shell is provided with an external thread, the connection cap is provided with an internal thread, and the connection cap is in threaded connection with the reaction module shell.

Specifically, the lower end of the sliding tube is provided with an observation notch, an observation window is arranged at a position of the lower seat shell corresponding to the observation notch, and a window is arranged at a position of the reaction module shell corresponding to the observation notch.

The present disclosure has the following advantages:

1. The solution box, the reagent reaction box, the reaction module shell, the reagent collection tube and the reagent collection tube plug of the reagent reaction module of the present disclosure can be changed, and are modularized to achieve the purpose of facilitating repeated test.
2. In the present disclosure, the upper end of the sliding tube are provided with two opposite chips, a gap is present between the two chips and the chips have elasticity, the bulges are clamped in the slots after the two chips are inserted into the fixed tube, at this moment, the gap between the two chips is larger than the thickness of the test paper, the test paper can be inserted into the fixed tube and the sliding tube through an opening in the top of the reaction module shell, the bulges departs from the slots when the sliding tube downwardly moves, than the inner wall of the fixed tube extrudes the bulges so that the two chips are close from each other so as to clamp the test paper, in such the way, the sliding tube can drive the test paper to downwardly move when downwardly moving, so the operation is convenient.
3. The device of the present disclosure adopts an isothermal amplification technology, that is, amplification is performed at the same temperature, which causes high reaction efficiency and greatly shortens the time of reaction; the isothermal amplification technology can obtain results in a shorter time compared with a PCR method; a special instrument is not needed, which greatly reduces the cost of operation; there is no need for training the professional operation, as well as electrophoresis or fluorescence detection, visualized results can be shown, and therefore the device is simple to use and convenient.

Figure 1:
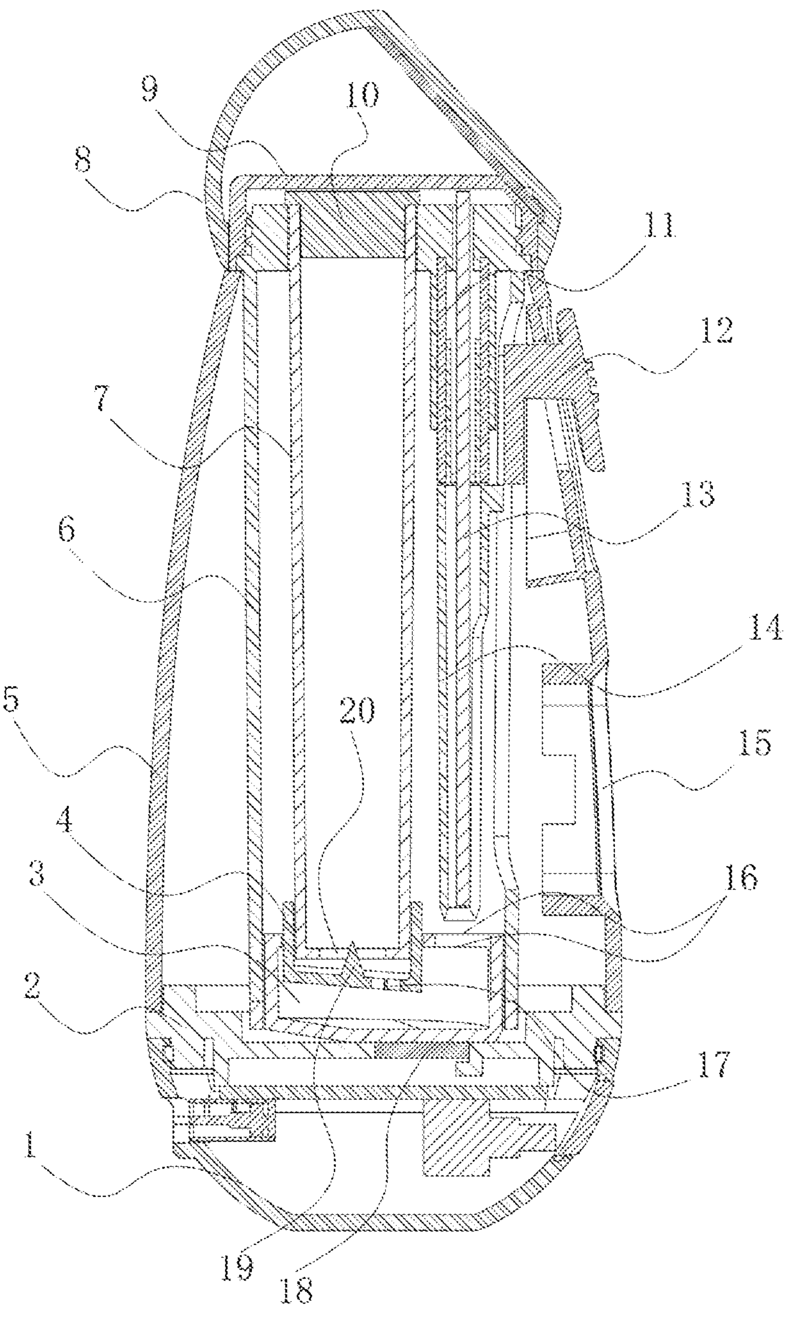
FIG. 1 is a sectional view of a test device structure of the present disclosure.

In the figures, 1—base; 2—heat-conducting plate; 3—solution box; 4—reagent reaction box; 5—lower seat shell; 6—reaction module shell; 7—reagent collection tube; 8—housing; 9—connection cap; 10—reagent collection tube plug; 11—fixed tube; 12—key; 13—test paper; 14—sliding tube; 15—observation window; 16—installation film; 17—leakage hole; 18—heating plate; 19—pointed cone; 20—film; 21—chute; 22—window; 23—observation notch; 24—chip; 25—stop block; 26—bulge.

DETAILED DESCRIPTION OF PREFERRED EMBODIMENTS

To make the purpose, technical solution and advantages of the present disclosure more clear, the present disclosure will be further described in detail in combination with drawings and embodiments below. It should be understood that specific embodiments described here are only for explaining but not limiting the present disclosure, that is, the described embodiments are only some embodiments of the present disclosure but not all the embodiments. Components of embodiments of the present disclosure described and illustrated in the drawings here can be generally arranged and designed in different configurations.

Therefore, the following detailed descriptions of the embodiments of the disclosure provided in the attached drawings are not intended to limit the protective scope of the disclosure, but only represent the selected embodiments of the present disclosure. Based on the embodiments of the present disclosure, all other embodiments obtained by those skilled in the art without creative efforts are all included within the protective scope of the present disclosure.

It should be noted that "first", "second" and other relational terms are only used to distinguish one entity or operation from another entity or operation, rather than necessarily requiring or implying any such actual relationship or order between these entities or operations. Moreover, the terms "comprising", "comprise" or any other variants thereof are intended to cover non exclusive inclusions, so that a process, method, article or device that comprises a series of elements comprise not only those elements, but also other elements not explicitly listed, or also comprise elements inherent to such process, method, article or device. Without further restrictions, the elements defined by the sentence "comprising a . . . " do not exclude the existence of other identical elements in the process, method, article or equipment that includes the elements.

Next, the disclosure will be further described in combination with the drawings, but the protective scope of the present disclosure is not limited to the following descriptions.

Figure 2:
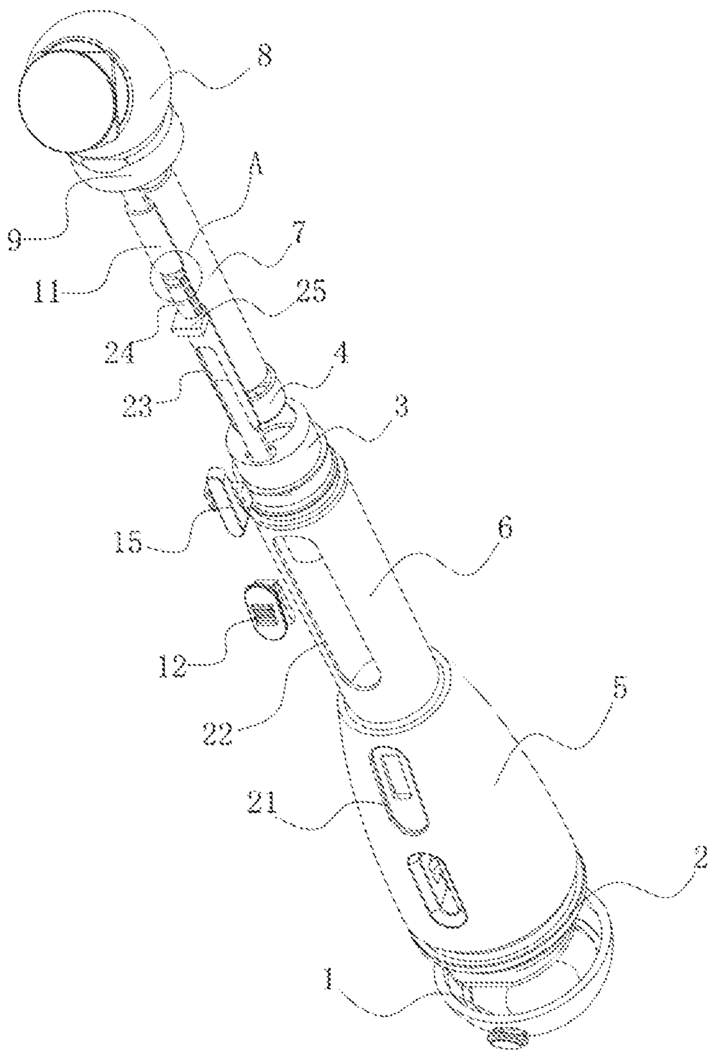
FIG. 2 is an exploded view of a test device structure of the present disclosure.
Figure 3:
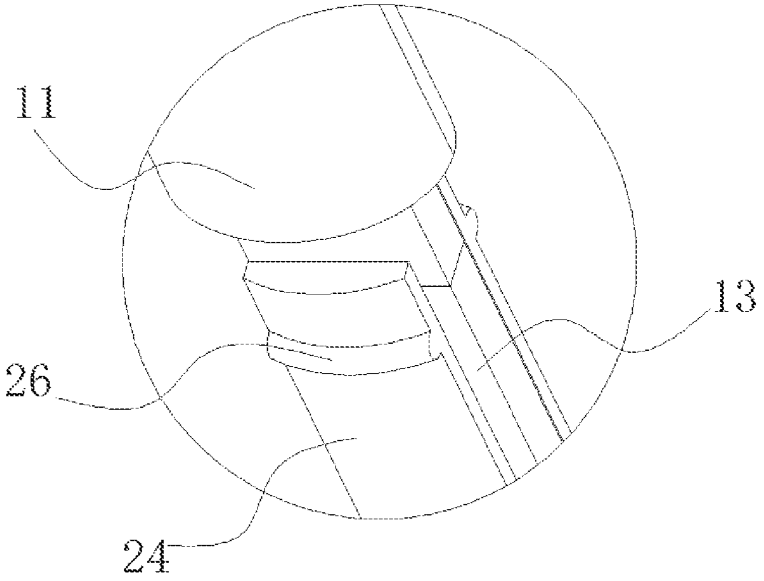
FIG. 3 is a diagram of an enlarged structure at A in FIG. 2.
Figure 4:
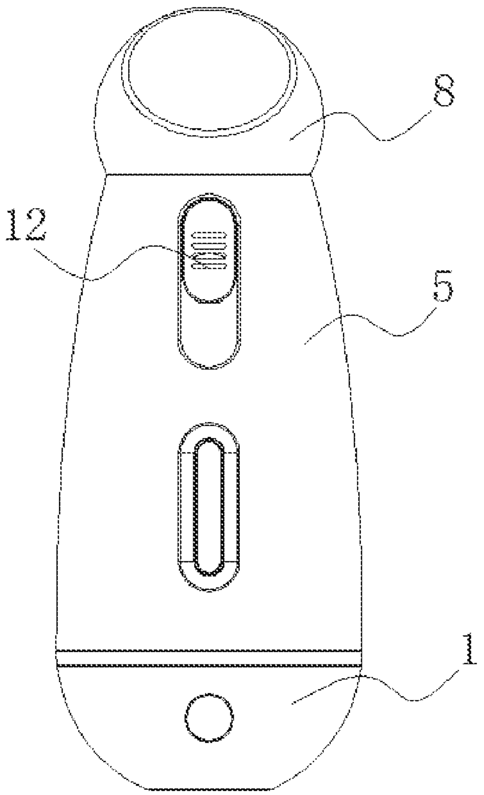
FIG. 4 is a diagram of an overall structure of the present disclosure.

As shown in FIG. 1-FIG. 4, a nucleic acid isothermal amplification colloidal gold test device comprises a lower seat and a reagent reaction module, wherein the reagent reaction module is slideably arranged in the lower seat, the reagent reaction module comprises a reaction module shell 6, a reagent collection tube 7, a reagent reaction box 4, a solution box 3 and a test paper installation assembly, the solution box 3 is arranged at the bottom of the reaction module shell 6 and located under the test paper installation assembly, the reagent reaction box 4 is arranged on the solution box 3 and partially located in the solution box 3, the reagent collection tube 7 is arranged in the reaction module shell 6 and the lower end is slideably matched with the reagent reaction box 4, the test paper installation assembly is arranged in the reaction module shell 6 and located outside the reagent collection tube 7.

In this example, the heating device is arranged in the lower seat, then the reagent reaction module is put in the lower seat, and the reagent reaction module is heated by the heating device in the lower seat for test. Specifically, the reagent reaction module is designed to a modularized structure, different tests are performed by changing the reagent reaction modules, the reaction module shell 6 is in a cylindrical structure, the lower end of the reaction module shell 6 is sleeved outside the solution box 3, the solution box 3 is bonded with the reaction module shell 6, the top of the solution box 6 is provided with a fixed hole, the reagent reaction box 4 is installed in the fixed hole, the reagent reaction box 4 is fixed together with the solution box 3, the solution box 3 is in a structure with an opening upper end, the top of the reaction module shell 6 is provided with a sliding hole, the reagent collection tube 7 is inserted into the reaction module shell 6 through the sliding hole, and the reagent collection tube 7 is downwardly pressed so that the lower end of the reagent collection tube 7 is inserted into the reagent reaction box 4. When in use, a specimen liquid to be tested is collected in the reagent collection tube 7 and then inserted into the reaction module shell 6, the reagent collection tube 7 is inserted into the reagent reaction box 4 and then the liquid in the reagent reaction tube 7 is introduced into the reagent reaction box 4 to react with a reaction enzyme in the reagent reaction box 4. After reaction, the liquid is introduced into the solution box 3, and the test paper 13 for test is installed in the test paper installation assembly. When in test, the test paper installation assembly drives the test paper 13 to downwardly move so that the test paper 13 is inserted into the solution box 3 to react with a medicament for test.

Further, the top of the reagent collection tube 7 is provided with a reagent collection tube plug 10. In this example, the top of the reagent collection tube 7 is provided with the reagent collection tube plug 10 to seal the reagent collection tube 7 to prevent the liquid in the reagent collection tube 7 from flowing out.

Further, the bottom of the reagent collection tube 7 is provided with a film 20, a pointed cone 19 is arranged at the bottom inside the reagent reaction box 4, and the bottom of the reagent reaction box 4 is provided with a leakage hole 17. In this example, the bottom of the reagent collection tube 7 is provided with a film 20 to seal the reagent collection tube 7 so that a liquid can be contained in the reagent collection tube 7, and a pointed cone 19 is arranged in the reagent reaction tube 4. When in test, the reagent collection tube 7 is inserted into the reaction module shell 6, and then downwardly pressed so that the film 20 at the bottom of the reagent collection tube 7 is in contact with the pointed cone 19, and the pointed cone 19 punctures the film 20, in such the way, the liquid in the reagent collection tube 7 flows into the reagent reaction box 4 to react with the reaction enzyme.

The bottom of the reagent reaction box 4 is provided with the leakage hole 17, the liquid after reaction flows into the solution box 3 through the leakage hole 17, and the solution box 3 is heated by the heating device in the lower seat so that the temperature of the solution in the solution box 3 is raised and this solution is maintained in a constant-temperature state, in such the way, the reaction and test can be performed.

Further, the test paper installation assembly comprises a fixed tube 11 and a sliding tube 14, the top end of the fixed tube 11 is fixed on the reaction module shell 6, and the upper end of the sliding tube 14 is slideably arranged in the fixed tube 11. In this example, the test paper installation assembly is needed to drive the test paper 13 to drop, an installation column is arranged on the reaction module shell 6 and is in a hollow structure, the fixed tube 11 is fixed in the installation column, the upper end of the sliding tube 14 is slideably connected with the fixed tube 11, the test paper 13 is inserted into the holes of the sliding tube 14 and the fixed tube 11, and the sliding tube 14 moves in the axial direction of the fixed tube 11 to drive the test paper 13 to downwardly move.

Further, the upper end of the sliding tube 14 is provided with two clips 24, the opposite outer sides of the two clips 24 are provided with bulges 26, and an inner wall in the fixed tube 11 is provided with slots matched with the bulges 26. In this example, the upper end of the sliding tube 14 is provided with two oppositely arranged clips 24, a gap is present between the two clips 24, and the clips 24 have elasticity. After the two clips 24 are inserted into the fixed tube 11, the bulges 26 are clamped in the slots, at this moment, the distance between the two clips 24 is greater than the thickness of the test paper 13. The test paper 13 can be inserted into the fixed tube 11 and the sliding tube 14 through the opening in the top of the reaction module shell 6. When the sliding tube 14 downwardly moves, the bulges 26 depart from the slots, then the inner wall of the fixed tube 11 extrudes the bulges 26 so that the two clips 24 are close from each other to clamp the test paper 1, in such the way, the sliding tube 14 can drive the test paper 13 to downwardly move when downwardly moving.

Further, the middle of the sliding tube 14 is provided with a stop block 25, a key 12 is slideably arranged on the lower seat, and the key 12 is matched with the stop block 25. In this example, the key 12 drives the sliding tube 14 to downwardly move, the key 12 is slideably installed on the lower seat, and an included angle is formed between the sliding path of the key 12 and the moving path of the sliding tube 14. When the sliding tube 14 needs to move to drive the movement of the test paper 13, the key 12 moves, and a press block is arranged on the key 12. When the key 12 moves, the press block is abutted against the stop block 25, and a force is applied to the stop block 25 to drive the sliding tube 14 to downwardly move, thereby driving the test paper 13 to move. After the key 12 moves to a certain distance, the press block departs from the stop block 25.

Further, an installation port is formed in a position of the solution box 3 corresponding to the reagent installation assembly, two layers of installation films 16 are arranged in the installation port, and a storage cavity is formed between two layers of the installation films 16. In this example, an installation port is formed in the solution box 3, and two layers of installation films 16 are arranged in the installation port. The storage cavity between two layers of the installation films 16 is filled with test reagents. When the test paper 13 downwardly moves, the force applied when the test paper 13 downwardly moves allows the test paper 13 to puncture two layers of installation films 16 so that the test reagent in the installation film flows into the solution box 3 to react with the solution in the solution box, and meanwhile the test paper strip is inserted into the solution box 3 to dilute the solution in the solution box 3 so as to achieve the test function.

Further, the lower seat comprises a seat bottom 1 and a lower seat shell 5, a heat-conducting plate 2 is arranged in the seat bottom 1, the heat-conducting plate 2 is provided with a heating plate 18, the lower seat shell 5 is arranged on the heat-conducting plate 2, and the bottom of the solution box 3 is in contact with the heating plate 18 and the heat-conducting plate 2. In this example, the seat bottom 1 is provided with a circuit board, the heating plate 18 is electrically connected with the circuit board, the seat bottom 1 is provided with a heating button, the heating button is electrically connected with the circuit board, the heating plate 18 is controlled through the heating button to heat the solution box 3, the heating button can also be arranged at the position of the key 12 to link to the button 12. When the key 12 is pressed, the heating button is triggered to heat, the heat-conducting plate 2 can be a metal plate, and the heat-conducting plate 2 is fixed on the seat bottom 1, the heating plate 18 is embedded on the heat-conducting plate 2. After heating, the heating plate 18 directly acts on the solution box 3 to heat the solution box 3, and then the heat of the heating plate 18 is transferred to the heat-conducting plate 2. The other parts of the solution box 3 are heated through the heat-conducting plate 2, the lower seat shell 5 is fixed on the heat-conducting plate 2, a chute 21 is arranged on the lower seat shell 5, and the key 12 is arranged in the chute 21; in this example, the reaction enzyme in the reagent reaction box 4 is Bts enzyme or other isothermal amplification enzymes, and a buffer solution is stored in the storage cavity formed between the installation films 16.

Further, the nucleic acid isothermal amplification colloidal gold test device further comprises a housing 8 and a connection cap 9, wherein the connection cap 9 is arranged in the housing 8, the upper end of the reaction module shell 6 is provided with an external thread 9, the connection cap 9 is provided with an internal thread, and the connection cap 9 is in threaded connection with the reaction module shell 6. In this example, the connection cap 9 is in a concave structure, the connection cap 9 is bonded in the housing 8, and the reagent collection tube 7 is limited between the connection cap 9 and the reaction module shell 6 through threaded connection with the reaction module shell 6.

Further, the lower end of the sliding tube 14 is provided with an observation notch 23, an observation window 15 is arranged at a position of the lower seat shell 5 corresponding to the observation notch 23, and a window 22 is arranged at a position of the reaction module shell 6 corresponding to the observation notch 23. In this example, to observe the structure tested by the test paper 13, the observation notch 23 is formed in the lower end of the sliding tube 14, the observation notch 23 corresponds to the window 22 and the observation window 15, in such the way, the test results of the test paper 13 can be observed through the observation window 15.

In conclusion, the above descriptions are only preferred embodiments of the present disclosure but not limiting the present disclosure in any forms. Many possible variations and modifications can be made to the technical solution of the present disclosure by those skilled in the art using the above technical solutions without departing from the scope of the technical solution of the present disclosure, or the technical solution of the present disclosure can be modified into equivalent embodiments with equivalent changes.

Therefore, any variations, amendments, equivalent changes and modifications made to the above technical solution according to the technology of the present disclosure without departing from the content of the technical solution of the present disclosure are all included within the protective scope of the technical solution of the present disclosure.

We claim:

1. A nucleic acid isothermal amplification colloidal gold test device, comprising a lower seat and a reagent module, wherein the reagent reaction module is slideably arranged in the lower seat, the reagent reaction module comprises a reaction module shell (6), a reagent collection tube (7), a reagent reaction box (4), a solution box (3) and a test paper installation assembly, the solution box (3) is arranged at the bottom of the reaction module shell (6) and located under the test paper installation assembly, the reagent reaction box (4) is arranged on the solution box (3) and partially located in the solution box (3), the reagent collection tube (7) is arranged in the reaction module shell (6) and the lower end is slideably matched with the reagent reaction box (4), and the test paper installation assembly is arranged in the reaction module shell (6) and located outside the reagent collection tube (7); and the reagent collection tube (7) being provided at the bottom with a film, a pointed cone (19) being arranged at the bottom inside the reagent reaction box (4); and the test paper installation assembly comprises a fixed tube (11) and a sliding tube (14), the top end of the fixed tube (11) is fixed on the reaction module shell (6), and the upper end of the sliding tube (14) is slideably arranged in the fixed tube (11), and a test paper being installed in the test installation assembly; and a heat-conducting plate (2) being arranged in the bottom of the lower seat, the heat-conducting plate (2) being provided with a heating plate (18) and the heat- conducting plate (2).

2. The nucleic acid isothermal amplification colloidal gold test device according to claim 1, wherein the top of the reagent collection tube (7) is provided with a reagent collection tube plug (10).

3. The nucleic acid isothermal amplification colloidal test device according to claim 1, wherein the bottom of the reagent reaction box (4) is provided with a leakage hole (17).

4. The nucleic acid isothermal amplification colloidal gold test the device according to claim 1, wherein the upper end of the sliding tube (14) is provided with two clips (24), the opposite outer sides of the two clips (24) are provided with bulges (26), and the inner wall of the fixed tube (11) is provided with slots matched with the bulges (26).

5. The nucleic acid isothermal amplification colloidal gold test the device according to claim 1, wherein the middle of the sliding tube (14) is provided with a stop block (25), a key (12) is slideably arranged on the lower seat, and the key (12) is matched with the stop block (25).

6. The nucleic acid isothermal amplification colloidal gold test the device according to claim 5, wherein an installation port is formed in a position of the solution box (3) corresponding to the reagent installation assembly, two layers of installation films (16) are arranged in the installation port, and a storage cavity is formed between two layers of the installation films (16).

7. The nucleic acid isothermal amplification colloidal gold test device according to claim 1, wherein the lower seat comprises a seat bottom (1) and a lower seat shell (5), the lower seat shell (5) is arranged on the heat- conducting plate (2).

8. The nucleic acid isothermal amplification colloidal gold test device according to claim 1, further comprising a housing (8) and a connection cap (9), wherein the connection cap (9) is arranged in the housing (8), the upper end of the reaction module shell (6) is provided with an external thread (9), the connection cap (9) is provided with an internal thread, and the connection cap (9) is in threaded connection with the reaction module shell (6).

9. The nucleic acid isothermal amplification colloidal gold test device according to claim 7, wherein the lower end of the sliding tube (14) is provided with an observation notch (23), an observation window (15) is arranged at a position of the lower seat shell (5) corresponding to the observation notch (23), and a window (22) is arranged at a position of the reaction module shell (6) corresponding to the observation notch (23).

* * * * *